United States Patent [19]
Goto et al.

[11] Patent Number: 5,776,858
[45] Date of Patent: Jul. 7, 1998

[54] 1-AZINYL-TETRAZOLINONES

[75] Inventors: Toshio Goto, Shimotsuga-gun; Seishi Ito, Tochigi; Natsuko Minegishi, Tochigi; Tatsuya Yamaoka, Oyama; Chieko Ueno, Tochigi; Koichi Moriya, Kawachigun; Fritz Maurer, Tochigi; Ryo Watanabe, Tochigi, all of Japan

[73] Assignee: Nihon Bayer Agrochem K.K., Tokyo, Japan

[21] Appl. No.: 736,867

[22] Filed: Oct. 25, 1996

[30] Foreign Application Priority Data

Oct. 31, 1995 [JP] Japan ................. 7-305187
Mar. 7, 1996 [JP] Japan ................. 8-78069

[51] Int. Cl.$^6$ .............. A01N 43/58; A01N 43/60; A01N 43/66; C07D 403/02
[52] U.S. Cl. .............. 504/225; 504/230; 504/235; 504/237; 504/239; 544/113; 544/114; 544/120; 544/122; 544/212; 544/238; 544/295; 544/316; 544/319; 544/320; 544/331; 544/333; 544/357; 544/382; 544/405
[58] Field of Search .............. 548/251; 544/212, 544/238, 333, 331, 405, 113, 114, 120, 122, 295, 318, 319, 320, 357, 382; 514/238, 243, 230; 504/225, 230, 239, 237

[56] References Cited

U.S. PATENT DOCUMENTS

| | | | |
|---|---|---|---|
| 4,618,365 | 10/1986 | Covey et al. | 548/251 |
| 4,826,529 | 5/1989 | Covey et al. | 548/251 |
| 4,830,661 | 5/1989 | Covey et al. | 548/251 |
| 5,003,075 | 3/1991 | Covey et al. | 549/251 |
| 5,019,152 | 5/1991 | Covey et al. | 548/251 |
| 5,342,954 | 8/1994 | Goto et al. | 548/251 |
| 5,344,814 | 9/1994 | Goto et al. | 548/251 |
| 5,347,009 | 9/1994 | Goto et al. | 548/251 |
| 5,347,010 | 9/1994 | Goto et al. | 548/251 |
| 5,362,704 | 11/1994 | Goto et al. | 548/253 |
| 5,502,204 | 3/1996 | Yanagi et al. | 548/251 |
| 5,530,135 | 6/1996 | Yanagi et al. | 548/251 |
| 5,589,439 | 12/1996 | Goto et al. | 504/261 |

FOREIGN PATENT DOCUMENTS

| | | |
|---|---|---|
| 146279 | 6/1985 | European Pat. Off. . |
| 0 638 561 A1 | 2/1995 | European Pat. Off. . |
| 0 643 049 A1 | 3/1995 | European Pat. Off. . |
| 0 646 577 | 4/1995 | European Pat. Off. . |
| 692482 | 1/1996 | European Pat. Off. . |
| 695748 | 2/1996 | European Pat. Off. . |
| 708097 | 4/1996 | European Pat. Off. . |
| 728750 | 8/1996 | European Pat. Off. . |

OTHER PUBLICATIONS

A.R. Bell, et al., British Crop Protecting Conference – Weeds, pp. 249–255 (1987).
G. Theodoridis, et al., Pestic. Sci., vol. 30, pp. 259–274 (1990).

Primary Examiner—Richard L. Raymond
Attorney, Agent, or Firm—Sprung Kramer Schaefer & Briscoe

[57] ABSTRACT

1-Azinyl-tetraozolinones of the following formulae (I) and (II):

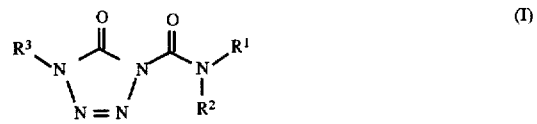

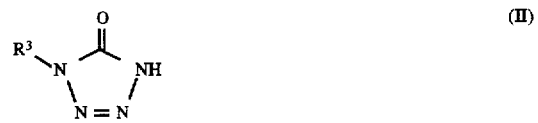

wherein
$R^1$ and $R^2$ are independently represent alkyl, haloalkyl, cycloalkyl, alkenyl, haloalkenyl, alkynyl or optionally substituted phenyl, or
$R^1$ and $R^2$, together with the nitrogen atom to which they are bonded, may form a 5- or 6-membered heterocyclic ring which may optionally contain a further heteroatom, and said heterocyclic ring may optionally be benzo-condensed and/or be substituted by one or more of $C_{1-4}$ alkyl(s), and
$R^3$ is a 6-membered heterocyclic aromatic group consisting of carbon atoms and 2 or 3 nitrogen atoms, which may optionally be substituted by halogen, $C_{1-4}$ alkyl, $C_{1-4}$ alkoxy, $C_{1-4}$ alkylthio, di($C_{1-4}$ alkyl)amino or phenyl.

The compounds of the formula (I) exhibit an excellent herbicidal activity and the compounds of the formula (II) are useful as starting materials in the production of the compounds of the formula (I).

10 Claims, No Drawings

1-AZINYL-TETRAZOLINONES

The present invention relates to 1-azinyl-tetrazolinones, to a process for the preparation thereof and to their use as herbicides, as well as novel intermediates for their preparation and to processes for their preparation.

It has been already known that a certain kind of tetrazolinone derivatives have herbicidal activity (see: Pestic. Sci. 1990, 30, 259–274; 1987 British Crop Protection Conference—Weeds 249–255, EP-A-146 279 (=U.S. Pat. Nos. 4,618,365, 4,826,529, 4,830,661, 4,956,469, 5,003,075 and 5 019 152); Japanese Patent Kokai Publications Hei 5-331153, Hei 5-331154, Hei 5-339249, Hei 6-199818, Hei 6-30601, Hei 7-97372 and Hei 7-258230).

There have been found novel compounds of the formula (I):

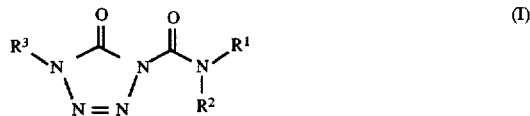

wherein
$R^1$ and $R^2$ are independently alkyl, haloalkyl, cycloalkyl, alkenyl, haloalkenyl, alkynyl or optionally substituted phenyl, or
$R^1$ and $R^2$, together with the nitrogen atom to which they are bonded, may form a 5- or 6-membered heterocyclic ring which may optionally contain a further heteroatom, and said heterocyclic ring may optionally be benzo-condensed and/or be substituted by one or more of $C_{1-4}$ alkyl(s), and $R^3$ is a 6-membered heterocyclic aromatic group consisting of carbon atoms and 2 or 3 nitrogen atoms, which may optionally be substituted by halogen, $C_{1-4}$ alkyl, $C_{1-4}$ alkoxy, $C_{1-4}$ alkylthio, di($C_{1-4}$ alkyl)amino or phenyl.

The novel compounds of the formula (I), according to the invention, can be obtained by a process in which
(a) compounds of the formula:

wherein $R^3$ has the same definition as above, are reacted with compounds of the formula:

wherein $R^1$ and $R^2$ have the same definitions as above and hal is a leaving group such as chlorine or bromine, in the presence of inert solvents, and, if appropriate, in the presence of an acid binder.

The compounds of formula (I), according to the invention, have strong herbicidal activities.

Surprisingly, the 1-azinyl-tetrazolinones of the above formula (I) provided by the invention, substantially exhibit extremely superior herbicidal activities as compared with those known from the prior art, for instance, the aforementioned EP-A-146 279 or the Japanese Patent Kokai Publications Hei 5-331 153, Hei 5-331 154, Hei 5-339 249, Hei 6-199 818, Hei 6-30 601, Hei 7-97 372 and Hei 7-258 230.

In the present specification, "halogen" and the halogen moiety in haloalkyl and haloalkoxy are fluorine, chlorine, bromine or iodine, preferably being chlorine or fluorine.

Alkyl may be straight-chain or branched and represents methyl, ethyl, propyl, isopropyl, n-, iso-, sec- or tert-butyl, n-, iso-, sec-, tert- or neo-pentyl, n-, iso-, sec-, tert- or neo-hexyl, etc.

Haloalkyl is the above-mentioned alkyl which is substituted by one or more halogen(s), and if substituted by a plurality of halogens, the halogens may be the same or different. Haloalkyl is, for example, trifluoromethyl, 2-chloroethyl, 2,2,2-trifluoroethyl, etc.

Cycloalkyl is, for example, cyclopropyl, cyclobutyl, cyclopentyl, cyclohexyl, cycloheptyl, cyclooctyl, etc.

Alkenyl is straight-chain or branched, e.g., vinyl, allyl, isopropenyl, 1-methyl-2-propenyl, 2- or 3-butenyl, 2-, 3- or 4-pentenyl, etc.

Haloalkenyl is the above-mentioned alkenyl which is substituted by one or more halogen(s), and if substituted by a plurality of halogens, the halogens may be the same or different. Haloalkenyl is, for instance, 2-chloro-2-propenyl, etc.

Alkynyl includes, for example, propargyl, etc.

Phenyl and the phenoxy may optionally be substituted. Examples of substituents thereof include halogen, cyano, nitro, alkyl, haloalkyl, alkoxy, haloalkoxy, alkylthio, etc.

The 5- or 6-membered heterocyclic ring contains at least one nitrogen atom as a hetero atom and may further contain hetero atom(s) selected from the group consisting of a nitrogen atom, an oxygen atom and a sulfur atom, and the heterocyclic ring may be benzo-condensed. Examples of such 5- or 6-membered heterocyclic rings include: pyrrolidinyl, 2,5-dimethylpyrrolidinyl, pyrrolinyl, 2,5-dimethylpyrrolinyl, imidazolidinyl, pyrazolidinyl, pyrazolinyl, piperidyl, 2-methylpiperidyl, 2,6-dimethylpiperidyl, piperazinyl, indolinyl, morpholinyl, 1,2,3,4-tetrahydroquinolyl, 2-methyl-1,2,3,4-tetrahydroquinolyl, etc.

Alkoxy may be straight-chain or branched and is, for example, methoxy, ethoxy, propoxy, isopropoxy, n-, iso-, sec- or tert-butoxy, n-, iso-, sec-, tert- or neo-pentoxy, n-, iso-, sec-, tert- or neo-hexoxy, etc.

Alkylthio includes, for example, methylthio, ethylthio, propylthio, isopropylthio, n-, iso-, sec- or tert-butylthio, n-, iso-, sec-, tert- or neo-pentylthio, n-, iso-, sec-, tert- or neo-hexylthio, etc.

The 6-membered heterocyclic aromatic group consisting of carbon atoms and 2 or 3 nitrogen atoms includes, for example, pyrimidinyl, pyrazinyl, pyridazinyl, 1,3,5-triazinyl, 1,2,4-triazinyl, etc. The 6-membered heterocyclic aromatic group may optionally be substituted, and examples of substituents thereof include halogen (fluorine, chlorine, bromine, etc.), cyano, nitro, alkyl (methyl, ethyl, propyl, etc.), haloalkyl (trifluoromethyl, etc.), alkoxy (methoxy, ethoxy, etc.), haloalkoxy (trifluoromethoxy, etc.), alkylthio (methylthio, ethylthio, etc.), dialkylamino (dimethylamino, diethylamino, etc.), and the like.

Among the 1-azinyl-tetrazolinones of the formula (I) according to the invention, preferred compounds are those, in which
$R^1$ and $R^2$ independently are $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl or phenyl, or
$R^1$ and $R^2$, together with the nitrogen atom to which they are bonded, form pyrrolidin-1-yl, 2,5-dimethyl pyrrolidin-1-yl, 3-pyrrolin-1-yl, 2,5-dimethyl-3-pyrrolin-1-yl, piperidino, 2-methylpiperidino, 2,6-dimethylpiperidino, piperazin-1-yl, morpholino, 1,2,3,4-tetrahydroquinolin-1-yl or 2-methyl-1,2,3,4- tetrahydroquinolin-1-yl, and
$R^3$ is pyrimidinyl, pyrazinyl, pyridazinyl or 1,3,5-triazinyl, which may optionally be substituted by chlorine, $C_{1-4}$ alkyl, $C_{1-4}$ alkoxy, $C_{1-4}$ alkylthio, di($C_{1-4}$ alkyl)amino or phenyl.

Amomg the compounds of the formula (I) according to the invention, more preferred compounds are those wherein $R^1$ and $R^2$ independently are $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl or phenyl, or $R^1$ and $R^2$, together with the nitrogen atom to which they are bonded, form pyrrolidin-1-yl, 2,5-dimethylpyrrolidin-1-yl, 3-pyrrolin-1-yl, 2,5-dimethyl-3-pyrrolin-1-yl, piperidino, 2-methylpiperidino, 2,6-dimethylpiperidino, piperazin-1-yl, morpholino, 1,2,3,4-tetrahydroquinolin-1-yl or 2-methyl-1,2,3,4-tetrahydroquinolin-1-yl, and $R^3$ is pyrimidinyl, pyrazinyl, pyridazinyl or 1,3,5-triazinyl, which may optionally be substituted by chlorine, methyl, methoxy, methylthio, dimethylamino or phenyl.

Examples of compounds of the formula (I), according to the invention, are set forth in the following Table 1 and Table 2, in addition to the compounds shown in the Synthesis Examples hereinbelow.

Table 1 shows compounds according to the invention where $R^1$ and $R^2$ represent independent groups. Table 2 shows compounds according to the invention where $R^1$ and $R^2$, together with the nitrogen atom to which they are bonded, form a heterocyclic ring. In Tables 1, 2 and 3, Q1 to Q15 represent the following groups, respectively.

| | |
|---|---|
| Q1: pyrimidin-2-yl, | Q2: pyrimidin-4-yl, |
| Q3: pyrimidin-5-yl, | Q4: pyrazin-2-yl, |
| Q5: pyridazin-3-yl, | Q6: 4-methylpyrimidin-5-yl, |
| Q7: 3-chloropyridazin-6-yl, | Q8: 4-methoxypyrimidin-6-yl, |
| Q9: 2-methylthiopyrimidin-4-yl, | Q10: 3-methoxypyridazin-6-yl, |
| Q11: 2-phenylpyrimidin-5-yl, | Q12: 4,6-dimethoxypyrimidin-2-yl, |
| Q13: 2,4-dimethylpyrimidin-5-yl, | Q14: 4,6-dimethoxypyrimidin-5-yl, |
| Q15: 2,4-dimethoxy-1,3,5-triazin-6-yl. | |

TABLE 1

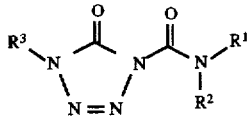

| $R^3$ | $R^1$ | $R^2$ |
|---|---|---|
| Q1 | methyl | methyl |
| Q1 | methyl | isopropyl |
| Q1 | methyl | cyclopropyl |
| Q1 | ethyl | ethyl |
| Q1 | ethyl | isopropyl |
| Q1 | ethyl | cyclopropyl |
| Q1 | ethyl | cyclohexyl |
| Q1 | n-propyl | isopropyl |
| Q1 | isopropyl | isopropyl |
| Q1 | isopropyl | phenyl |
| Q2 | methyl | ethyl |
| Q2 | methyl | isopropyl |
| Q2 | methyl | cyclopropyl |
| Q2 | ethyl | ethyl |
| Q2 | ethyl | isopropyl |
| Q2 | ethyl | cyclopropyl |
| Q2 | ethyl | cyclohexyl |
| Q2 | n-propyl | isopropyl |
| Q2 | isopropyl | isopropyl |
| Q2 | isopropyl | phenyl |
| Q3 | methyl | methyl |
| Q3 | methyl | isopropyl |
| Q3 | methyl | cyclopropyl |
| Q3 | ethyl | ethyl |
| Q3 | ethyl | isopropyl |
| Q3 | ethyl | cyclopropyl |
| Q3 | ethyl | cyclohexyl |

TABLE 1-continued

| $R^3$ | $R^1$ | $R^2$ |
|---|---|---|
| Q3 | n-propyl | isopropyl |
| Q3 | isopropyl | isopropyl |
| Q3 | isopropyl | phenyl |
| Q4 | methyl | ethyl |
| Q4 | methyl | isopropyl |
| Q4 | methyl | cyclopropyl |
| Q4 | ethyl | ethyl |
| Q4 | ethyl | isopropyl |
| Q4 | ethyl | cyclopropyl |
| Q4 | ethyl | cyclohexyl |
| Q4 | n-propyl | isopropyl |
| Q4 | isopropyl | phenyl |
| Q5 | methyl | methyl |
| Q5 | methyl | isopropyl |
| Q5 | methyl | cyclopropyl |
| Q5 | ethyl | ethyl |
| Q5 | ethyl | isopropyl |
| Q5 | ethyl | cyclopropyl |
| Q5 | ethyl | cyclohexyl |
| Q5 | n-propyl | isopropyl |
| Q5 | isopropyl | isopropyl |
| Q5 | isopropyl | phenyl |
| Q6 | methyl | methyl |
| Q6 | methyl | ethyl |
| Q6 | methyl | n-propyl |
| Q6 | methyl | isopropyl |
| Q6 | methyl | cyclopropyl |
| Q6 | methyl | s-butyl |
| Q6 | methyl | t-butyl |
| Q6 | methyl | cyclopentyl |
| Q6 | methyl | cyclohexyl |
| Q6 | methyl | phenyl |
| Q6 | methyl | 1-methyl-2-propenyl |
| Q6 | ethyl | ethyl |
| Q6 | ethyl | n-propyl |
| Q6 | ethyl | isopropyl |
| Q6 | ethyl | 2,2,2-trifluoroethyl |
| Q6 | n-propyl | 2,2,2-trifluoroethyl |
| Q6 | isopropyl | 2,2,2-trifluoroethyl |
| Q6 | 2-chloroethyl | ethyl |
| Q6 | 2-chloroethyl | n-propyl |
| Q6 | 2-chloroethyl | isopropyl |
| Q6 | 2-chloroethyl | 2-chloroethyl |
| Q6 | ethyl | cyclopropyl |
| Q6 | ethyl | s-butyl |
| Q6 | ethyl | cyclopentyl |
| Q6 | ethyl | cyclohexyl |
| Q6 | ethyl | phenyl |
| Q6 | n-propyl | isopropyl |
| Q6 | n-propyl | cyclopropyl |
| Q6 | n-propyl | s-butyl |
| Q6 | n-propyl | cyclopentyl |
| Q6 | n-propyl | cyclohexyl |
| Q6 | isopropyl | isopropyl |
| Q6 | isopropyl | cyclohexyl |
| Q6 | isopropyl | phenyl |
| Q6 | isopropyl | allyl |
| Q6 | isopropyl | 2-chloro-2-propenyl |
| Q6 | isopropyl | 2-chloro-2-propenyl |
| Q6 | isopropyl | propargyl |
| Q6 | allyl | allyl |
| Q6 | propargyl | propargyl |
| Q7 | methyl | methyl |
| Q7 | methyl | ethyl |
| Q7 | methyl | isopropyl |
| Q7 | methyl | cyclopropyl |
| Q7 | methyl | t-butyl |
| Q7 | methyl | phenyl |
| Q7 | ethyl | ethyl |
| Q7 | ethyl | isopropyl |

TABLE 1-continued

| R³ | R¹ | R² |
|---|---|---|
| Q7 | ethyl | cyclopropyl |
| Q7 | ethyl | cyclohexyl |
| Q7 | ethyl | 2,2,2-trifluoroethyl |
| Q7 | 2-chloroethyl | ethyl |
| Q7 | n-propyl | isopropyl |
| Q7 | n-propyl | cyclopropyl |
| Q7 | isopropyl | isopropyl |
| Q7 | isopropyl | cyclohexyl |
| Q7 | isopropyl | phenyl |
| Q7 | isopropyl | allyl |
| Q7 | propargyl | propargyl |
| Q8 | methyl | cyclopropyl |
| Q8 | methyl | t-butyl |
| Q8 | methyl | cyclohexyl |
| Q8 | methyl | 1-methyl-2-propenyl |
| Q8 | ethyl | ethyl |
| Q8 | ethyl | n-propyl |
| Q8 | ethyl | isopropyl |
| Q8 | ethyl | cyclopentyl |
| Q8 | n-propyl | s-butyl |
| Q8 | isopropyl | isopropyl |
| Q8 | isopropyl | phenyl |
| Q8 | isopropyl | allyl |
| Q9 | methyl | isopropyl |
| Q9 | methyl | cyclopropyl |
| Q9 | methyl | s-butyl |
| Q9 | methyl | cyclohexyl |
| Q9 | ethyl | ethyl |
| Q9 | ethyl | n-propyl |
| Q9 | ethyl | cyclopropyl |
| Q9 | ethyl | cyclohexyl |
| Q9 | n-propyl | isopropyl |
| Q9 | n-propyl | cyclopropyl |
| Q9 | isopropyl | isopropyl |
| Q9 | isopropyl | phenyl |
| Q9 | isopropyl | allyl |
| Q10 | methyl | methyl |
| Q10 | methyl | ethyl |
| Q10 | methyl | isopropyl |
| Q10 | methyl | cyclopropyl |
| Q10 | methyl | t-butyl |
| Q10 | ethyl | ethyl |
| Q10 | ethyl | n-propyl |
| Q10 | ethyl | isopropyl |
| Q10 | ethyl | cyclopropyl |
| Q10 | ethyl | cyclohexyl |
| Q10 | ethyl | phenyl |
| Q10 | n-propyl | isopropyl |
| Q10 | n-propyl | cyclopropyl |
| Q10 | isopropyl | phenyl |
| Q10 | isopropyl | allyl |
| Q11 | methyl | ethyl |
| Q11 | methyl | isopropyl |
| Q11 | ethyl | ethyl |
| Q11 | ethyl | isopropyl |
| Q11 | ethyl | cyclopropyl |
| Q11 | ethyl | cyclohexyl |
| Q11 | n-propyl | isopropyl |
| Q11 | n-propyl | cyclopropyl |
| Q11 | isopropyl | isopropyl |
| Q11 | isopropyl | phenyl |
| Q11 | isopropyl | allyl |
| Q12 | methyl | ethyl |
| Q12 | methyl | isopropyl |
| Q12 | methyl | cyclopropyl |
| Q12 | methyl | s-butyl |
| Q12 | methyl | t-butyl |
| Q12 | methyl | cyclohexyl |
| Q12 | methyl | phenyl |
| Q12 | methyl | 1-methyl-2-propenyl |
| Q12 | ethyl | ethyl |
| Q12 | ethyl | isopropyl |
| Q12 | ethyl | cyclopropyl |
| Q12 | ethyl | cyclohexyl |
| Q12 | n-propyl | isopropyl |
| Q12 | n-propyl | cyclopropyl |
| Q12 | n-propyl | cyclohexyl |
| Q12 | isopropyl | isopropyl |
| Q12 | isopropyl | phenyl |
| Q12 | isopropyl | allyl |
| Q13 | methyl | methyl |
| Q13 | methyl | ethyl |
| Q13 | methyl | n-propyl |
| Q13 | methyl | isopropyl |
| Q13 | methyl | t-butyl |
| Q13 | methyl | cyclopentyl |
| Q13 | methyl | cyclohexyl |
| Q13 | methyl | 1-methyl-2-propenyl |
| Q13 | ethyl | ethyl |
| Q13 | ethyl | n-propyl |
| Q13 | ethyl | isopropyl |
| Q13 | ethyl | cyclopropyl |
| Q13 | ethyl | cyclohexyl |
| Q13 | ethyl | phenyl |
| Q13 | ethyl | 2,2,2-trifluoroethyl |
| Q13 | isopropyl | 2,2,2-trifluoroethyl |
| Q13 | 2-chloroethyl | ethyl |
| Q13 | 2-chloroethyl | isopropyl |
| Q13 | 2-chloroethyl | 2-chloroethyl |
| Q13 | n-propyl | isopropyl |
| Q13 | n-propyl | cyclopropyl |
| Q13 | isopropyl | isopropyl |
| Q13 | isopropyl | cyclohexyl |
| Q13 | isopropyl | phenyl |
| Q13 | isopropyl | allyl |
| Q13 | isopropyl | 2-chloro-2-propenyl |
| Q13 | isopropyl | 2-methyl-2-propenyl |
| Q13 | isopropyl | propargyl |
| Q13 | allyl | allyl |
| Q13 | propargyl | propargyl |
| Q14 | methyl | methyl |
| Q14 | methyl | ethyl |
| Q14 | methyl | n-propyl |
| Q14 | methyl | isopropyl |
| Q14 | methyl | cyclopropyl |
| Q14 | methyl | s-butyl |
| Q14 | methyl | t-butyl |
| Q14 | methyl | cyclopentyl |
| Q14 | methyl | cyclohexyl |
| Q14 | methyl | phenyl |
| Q14 | methyl | 1-methyl-2-propenyl |
| Q14 | ethyl | ethyl |
| Q14 | ethyl | n-propyl |
| Q14 | ethyl | isopropyl |
| Q14 | ethyl | cyclopropyl |
| Q14 | ethyl | s-butyl |
| Q14 | ethyl | cyclopentyl |
| Q14 | ethyl | cyclohexyl |
| Q14 | ethyl | phenyl |
| Q14 | ethyl | 2,2,2-trifluoroethyl |
| Q14 | n-propyl | 2,2,2-trifluoroethyl |
| Q14 | isopropyl | 2,2,2-trifluoroethyl |
| Q14 | 2-chloroethyl | ethyl |
| Q14 | 2-chloroethyl | n-propyl |
| Q14 | 2-chloroethy | isopropyl |
| Q14 | 2-chloroethyl | 2-chloroethyl |
| Q14 | n-propyl | isopropyl |
| Q14 | n-propyl | cyclopropyl |
| Q14 | n-propyl | s-butyl |
| Q14 | n-propyl | cyclopentyl |

TABLE 1-continued structure with $R^3$-N, N=N, and carbonyl-N-carbonyl-N(R^1)(R^2)

| $R^3$ | $R^1$ | $R^2$ |
|---|---|---|
| Q14 | n-propyl | cyclohexyl |
| Q14 | isopropyl | isopropyl |
| Q14 | isopropyl | cyclohexyl |
| Q14 | isopropyl | phenyl |
| Q14 | isopropyl | allyl |
| Q14 | isopropyl | 2-chloro-2-propenyl |
| Q14 | isopropyl | 2-methyl-2-propenyl |
| Q14 | isopropyl | propargyl |
| Q14 | allyl | allyl |
| Q14 | propargyl | propargyl |
| Q15 | methyl | n-propyl |
| Q15 | methyl | isopropyl |
| Q15 | methyl | cyclopropyl |
| Q15 | methyl | s-butyl |
| Q15 | methyl | phenyl |
| Q15 | methyl | 1-methyl-2-propenyl |
| Q15 | ethyl | ethyl |
| Q15 | ethyl | n-propyl |
| Q15 | ethyl | isopropyl |
| Q15 | ethyl | cyclopropyl |
| Q15 | isopropyl | 2,2,2-trifluoroethyl |
| Q15 | n-propyl | isopropyl |
| Q15 | n-propyl | cyclopropyl |
| Q15 | isopropyl | isopropyl |
| Q15 | isopropyl | cyclohexyl |
| Q15 | isopropyl | phenyl |
| Q15 | isopropyl | allyl |
| Q15 | allyl | allyl |

TABLE 2

| $R^3$ | |
|---|---|
| Q6 | pyrrolidin-1-yl |
| Q6 | piperidin-1-yl (= piperidino) |
| Q6 | morpholino |
| Q6 | 2-methylpiperidin-1-yl |
| Q6 | 2,5-dimethylpyrrolidin-1-yl |
| Q6 | 2,6-dimethylpiperidin-1-yl |
| Q6 | 2-methyl-1,2,3,4-tetrahydroquinolin-1-yl |
| Q7 | piperidin-1-yl |
| Q7 | morpholino |
| Q7 | 2,5-dimethylpyrrolidin-1-yl |
| Q7 | 2,6-dimethylpiperidin-1-yl |
| Q8 | piperidin-1-yl |
| Q8 | morpholino |
| Q8 | 2,5-dimethylpyrrolidin-1-yl |
| Q9 | pyrrolidin-1-yl |
| Q9 | piperidin-1-yl |
| Q9 | morpholino |
| Q10 | pyrrolidin-1-yl |
| Q10 | piperidin-1-yl |
| Q10 | morpholino |
| Q12 | 2-methylpiperidin-1-yl |
| Q12 | 2,5-dimethylpyrrolidin-1-yl |
| Q12 | 2,6-dimethylpiperidin-1-yl |
| Q12 | 2-methyl-1,2,3,4-tetrahydroquinolin-1-yl |

TABLE 2-continued

| $R^3$ | |
|---|---|
| Q13 | pyrrolidin-1-yl |
| Q13 | piperidin-1-yl |
| Q13 | morpholino |
| Q13 | 2-methylpiperidin-1-yl |
| Q13 | 2,5-dimethylpyrrolidin-1-yl |
| Q13 | 2,6-dimethylpiperidin-1-yl |
| Q13 | 2-methyl-1,2,3,4-tetrahydroquinolin-1-yl |
| Q14 | pyrrolidin-1-yl |
| Q14 | piperidin-1-yl |
| Q14 | morpholino |
| Q14 | 2-methylpiperidin-1-yl |
| Q14 | 2,5-dimethylpyrrolidin-1-yl |
| Q14 | 2,6-dimethylpiperidin-1-yl |
| Q14 | 2-methyl-1,2,3,4-tetrahydroquinolin-1-yl |

When in the process (a), for example, 1-(5-pyrimidyl)-5 (4H)-tetrazolinone and diethylcarbamoyl chloride are used as the starting materials, the course of the reaction is as follows:

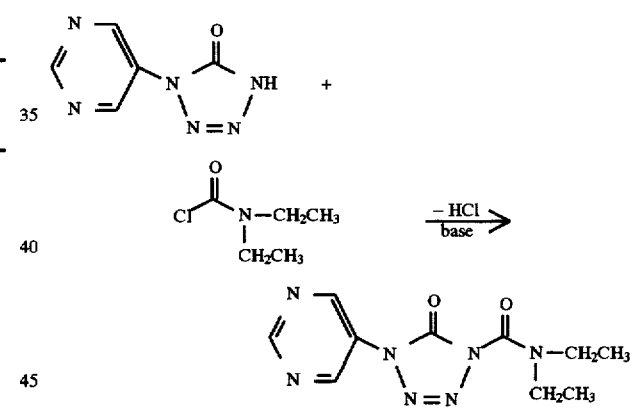

In the starting compounds of formula (II), employed in process (a), $R^3$ has the same meanings and preferred meanings as defined above for $R^3$ in formula (I).

The compounds of the formula (II), used as the starting materials in the process (a), are novel compounds, and can be obtained by the following processes:

(b) compound of the formula:

wherein $R^3$ is defined as above,
are reacted with trimethylsilyl azide, followed by subjecting the reaction product to hydrolysis with water or alcohols, or (c) compounds of the formula:

wherein $R^3$ is defined as above, are reacted with trimethylsilyl azide, if appropriate, in the presence of catalysts,
or
(d) compounds of the formula:

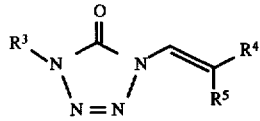

(VI)

wherein $R^3$ is defined as above, and $R^4$ and $R^5$ independently of one another represents $C_{1-4}$ alkyl,
are reacted with osmium tetraoxide and then reacted with sodium periodate, in the presence of protic solvents.

The compounds of the formula (IV), used as starting materials in the above precess (b), are well known in the field of organic chemistry (commercially available in general as a reagent or the production method thereof is known in the literature), or the compounds of the formula (IV) can easily be obtained by reacting a compound of the formula:

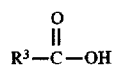

(VII)

wherein $R^3$ is defined as above,
with a halogenating agent (e.g. thionyl chloride).

The compounds of the above formula (VII) are well known in the field of organic chemistry. Examples of compounds of the formula (VII) include the following:

5-carboxypyrimidine, 5-carboxy-2,4-dimethoxypyrimidine, etc.

The reaction in the above process (b) can be carried out according to the method for synthesizing tetrazolinones described in Journal of the Chemical Society, Perkin Transactions 1, 1992, pp 1101–1104 or in The Journal of American Chemical Society, 81(7), pp 3076–3079 (1959).

The compounds of the formula (V), used as starting materials in the above process (c), are well known in the field of organic chemistry, or the compounds of the formula (V) can be produced by reacting a compound of the formula (VIII):

(VIII)

wherein $R^3$ is defined as above,
with phosgene or diphosgene. This reaction is well known in the field of organic chemistry and can be carried out, for example, according to the method described in "Experimental Chemistry Course (Jikken Kagaku Koza), the fourth edition" edited by Japanese Chemical Society, Vol. 14-II, pp 1491 (1992) issued by Maruzen.

Examples of compounds of the formula (VIII) include the following:

5-aminopyrimidine, 5-amino-2-phenylpyrimidine, 5-amino-2,4-dimethylpyrimidine, 5-amino-4,6-dimethoxypyrimidine, and others.

Examples of compounds of the formula (V) include the following:

5-isocyanatopyrimidine, 5-isocyanato-2-phenylpyrimidine, 5-isocyanato-2,4-dimethylpyrimidine, 5-isocyanato-4,6-dimethoxypyrimidine, and others.

The reaction in the process (c) can be carried out, for example, according to the method for synthesizing tetrazolinones described in Japanese Patent Kokai Publication Hei 7-97 372.

The compounds of the formula (VI), used as starting materials in the above process (d), can be produced, for example, by the following method (f).

(f) compounds of the formula:

$R^3$—X (IX)

wherein $R^3$ is defined as above, and X represents a leaving group such as halogen or methylsulfonyl,
are reacted with compounds of the formula:

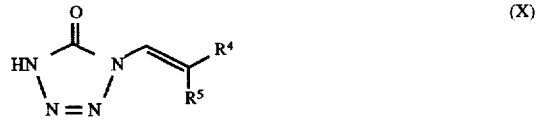

(X)

wherein $R^4$ and $R^5$ are defined as above,
in the presence of inert solvents, and, if appropriate, in the presence of acid binders.

The compounds of the formula (IX), used as starting materials in the above process (f), are well known in the field of organic chemistry and examples thereof include the following:

2-methylsulfonylpyrimidine, 4-methylsulfonylpyrimidine, 4,5-dichloropyrimidine, 4-chloro-5-methylpyrimidine, 3-methylsulfonylpyridazine, 2-methylsulfonylpyrazine, 4,6-dimethoxy-2-methylsulfonylpyrimidine, 2-chloro-4,6-dimethoxy-1,3,5-triazine, 2,4-dichloro-6-dimethylamino-1,3,5-triazine, and others.

On the other hand, the compounds of the formula (X), used as starting materials in the above process (f), can be synthesized by a method similar to those of the above processes (b) or (c). Namely, the compounds of the formula (X) can be obtained by the following processes:

(h) by reacting a compound represented by the following formula (XI):

(XI)

wherein $R^4$ and $R^5$ are defined as above,
with trimethylsilyl azide in the presence of a catalytic amount of boron trifluoride-ether complex, followed by subjecting the reaction product to hydrolysis with water or alcohols,
or (i) by reacting a compound of the above formula (XI) with sodium azide,
in protic solvents in the presence of a catalytic amount of ammonium chloride;
or (j) by reacting a compound of the formula (XII):

(XII)

wherein $R^4$ and $R^5$ are defined as above,
with trimethylsilyl azide, followed by subjecting the reaction product to hydrolysis with water or alcohols.

The compounds of the formula (XI), used as the starting materials in the above processes (h) and (i), are isocyanates which are well known in the field of organic chemistry and can be produced, for example, using a method analogous to that described in "Method for Synthesizing Organic Compounds (Yuki Kagobutsu Goseiho)" edited by Organice Chemical Society, Vol. 11, pp 133 (Issued by an incorporated body, Gihodo, on Jul. 15, 1959), i.e., via alkenecarbonyl azide which is obtainable by reacting the corresponding alkenecarboxylic acid chloride with sodium azide.

The compounds of the formula (XII), used as the starting materials in the above process (j), include acid chlorides which are known in the field of organic chemistry and can easily be obtained using a method ananlogous to that described in "New Experimental Chemistry Course (Shin Jikken Kagaku Koza)", Vol. 14, pp 1105–1120 (Issued by Maruzen on Dec. 20, 1977), i.e., by reacting an alkenecarboxylic acid of the formula:

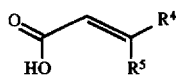

wherein $R^4$ and $R^5$ are defined as above,
with a halogenating agent (e.g. thionyl chloride).

The compounds of the above formula (XIII) can easily be obtained by hydrolyzing the corresponding alkenecarboxylic acid ester, according to a method analogous to that described in "New Experimental Chemistry Course (Shin Jikken Kagaku Koza)", Vol. 14, pp 921–1000 (Issued by Maruzen on Dec. 20, 1977).

In the starting compounds of formula (III), employed in process (a), $R^1$ and $R^2$ have the same meanings and preferred meanings as defined above for $R^1$ and $R^2$ in formula (I).

The compounds of the formula (III), used as the starting material in the above process (a), are well known in the field of organic chemistry or commercially available as reagents, and examples thereof include the following compounds:

diisopropyl carbamoyl chloride (and bromide),
diethyl carbamoyl chloride (and bromide),
dimethyl carbamoyl chloride (and bromide),
N-methyl-N-ethyl carbamoyl chloride (and bromide),
N-methyl-N-n-propyl carbamoyl chloride (and bromide),
N-methyl-N-isopropyl carbamoyl chloride (and bromide),
N-methyl-N-cyclopropyl carbamoyl chloride (and bromide),
N-methyl-N-s-butyl carbamoyl chloride (and bromide),
N-methyl-N-cyclopentyl carbamoyl chloride (and bromide),
N-methyl-N-cyclohexyl carbamoyl chloride (and bromide),
N-methyl-N-phenyl carbamoyl chloride (and bromide),
N-methyl-N-1-methyl-2-propenyl carbamoyl chloride (and bromide),
N-ethyl-N-n-propyl carbamoyl chloride (and bromide),
N-ethyl-N-isopropyl carbamoyl chloride (and bromide),
N-ethyl-N-cyclopropyl carbamoyl chloride (and bromide),
N-ethyl-N-s-butyl carbamoyl chloride (and bromide),
N-ethyl-N-cyclopentyl carbamoyl chloride (and bromide),
N-ethyl-N-cyclohexyl carbamoyl chloride (and bromide),
N-ethyl-N-phenyl carbamoyl chloride (and bromide),
N-n-propyl-N-isopropyl carbamoyl chloride (and bromide),
N-n-propyl-N-cyclopropyl carbamoyl chloride (and bromide),
N-n-propyl-N-s-butyl carbamoyl chloride (and bromide),
N-n-propyl-N-cyclopentyl carbamoyl chloride (and bromide),
N-n-propyl-N-cyclohexyl carbamoyl chloride (and bromide),
N-isopropyl-N-cyclohexyl carbamoyl chloride (and bromide),
N-isopropyl-N-phenyl carbamoyl chloride (and bromide),
N-isopropyl-N-allyl carbamoyl chloride (and bromide),
N-isopropyl-N-propargyl carbamoyl chloride (and bromide),
N-isopropyl-N-(2-chloro-2-propenyl) carbamoyl chloride (and bromide),
N-isopropyl-N-(2-methyl-2-propenyl) carbamoyl chloride (and bromide),
N,N-diallyl carbamoyl chloride (and bromide),
N,N-dipropargyl carbamoyl chloride (and bromide),
N,N-di(2-chloroethyl) carbamoyl chloride (and bromide),
morpholino carbonyl chloride (and bromide),
2-methylpiperidino carbonyl chloride (and bromide),
2,5-dimethylpyrrolidine-1-yl carbonyl chloride (and bromide),
2,6-dimethylpiperidino carbonyl chloride (and bromide),
2-methyl-1,2,3,4-tetrahydroquinon-1-yl carbonyl chloride (and bromide),
pyrrolidine-1-yl carbonyl chloride (and bromide),
piperidino carbonyl chloride (and bromide),
2,5-dimethyl-3-pyrrolin-1-yl carbonyl chloride (and bromide), and others.

The reaction in the above method (a) can be carried out, for example, according to the method for producing tetrazolinones described in Japanese Patent Kokai Publication Hei 7-118 246.

The reaction in the above method (a) may be carried out in an appropriate diluent. Examples of useful diluents include aliphatic, alicyclic and aromatic hydro-carbons (which may optionally be chlorinated) such as pentane, hexane, cyclohexane, petroleum ether, ligroin, benzene, toluene, xylene, dichloromethane, chloroform, carbon tetrachloride, 1,2-clichloroethane, chlorobenzene and dichlorobenzene; ethers such as diethyl ether, methyl t-butyl ether, di-isopropyl ether, dibutyl ether, dioxane, dimethoxyethane (DME), tetrahydrofuran (THF) and diethyleneglycol dimethyl ether (DGM); nitriles such as acetonitirile and propionitrile; acid amides such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides such as dimethylsulfoxide (DMSO) and sulfolane; bases such as pyridine; and others.

The method (a) can be carried out in the presence of an acid binding agent and useful acid binding agents are exemplified by inorganic bases such as hydroxides, carbonates, bicarbonates and alcoholatos of alkali metals or alkaline earth metals including sodium hydrogen carbonate, potassium hydrogen carbonate, sodium carbonate, potassium carbonate, lithium hydroxide, sodium hydroxide, potassium hydroxide, calcium hydroxide, sodium methoxide, potassium methoxide, potassium tert-butoxide and the like; inorganic alkali metal amides including lithium amides, sodium amide, potassium amide and the like; and organic bases such as tertiary amines, dialkylaminoanilines and pyridines including triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2.2.2]octane (DABCO), 1,8-diazabicyclo[5,4,0]undec-7-ene (DBU) and the like; such as organic lithium compounds including methyl lithium, n-butyl lithium, sec-butyl lithium, tert-butyl lithium, phenyl lithium, dimethyl copper lithium, lithium diisopropylamide, lithium cyclohexyl isopropylamide, lithium dicyclohexylamide, n-butyl lithium.DABCO, n-butyl lithium.DBU, n-butyl lithium.TMEDA, and the like.

The reaction in method (a) can be conducted substantially at temperatures within a broad range but it is preferable to carry it out generally in the temperature range of about −30° to about 200° C., preferably about −20° to about 130° C. Also, the reaction can be carried out under atmospheric pressure but may also be optionally operated under elevated or reduced pressure.

The method (a) can be carried out by reacting, for example, 1 to 1.5 mols of the compound of the formula (III) with 1 mol of the compound of formula (II), in a diluent (such as toluene), in the presence of 1 to 1.5 mols of an acid binding agent, thereby to obtain the desired compound of the formula (I).

The active compounds according to the invention can be used as defoliants, desiccants, agents for destroying broad-leaved plants and, especially, as weedkillers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents, diluents or carriers, there are suitable, in the main, aromatic hydrocarbons, such as xylene, toluene or alkyl napthalenes, chlorinated aromatic or chlorinated aliphatic hydrocarbons, such as chloro-benzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dye stuffs, azo dye stuffs or metal phthalocyanine dye stuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.001 and 10 kg of active compound per hectare of soil surface, preferably between 0.01 and 5 kg per ha.

The preparation and use of the active compounds according to the invention can be seen from the following examples.

SYNTHESIS EXAMPLE 1

(Synthesis of a Compound of Formula (I))

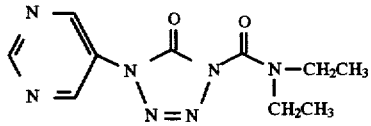

1-(5-Pyrimidyl)-5(4H)-tetrazolinone (1.0 g), diethylcarbamoyl chloride (0.9 g) and 4-dimethylamino-pyridine (0.9 g) were suspended in acetonitrile (15 ml) and the mixture was heated under stirring at 60° C. for 6 hours. After a salt was removed by filtration, the solvent was distilled off under reduced pressure, and the residue was subjected to silica gel column chromatography (eluant: chloroform) to obtain 1-(5-pyrimidyl)-4-(N,N-diethylcarbamoyl)-5(4H)-tetrazolinone (0.9 g).

mp. 56°–58° C.

The compounds shown in the following Table 3 were obtained by methods similar to that of the above Synthesis Example 1. The compound of Synthesis Example 1 is also shown in Table 3.

TABLE 3

| Compound No. | R³ | R¹ | R² | physical constant |
|---|---|---|---|---|
| 1 | Q3 | ethyl | ethyl | mp. 56–58° C. |
| 2 | Q3 | ethyl | cyclohexyl | mp. 90–92.5° C. |
| 3 | Q3 | isopropyl | isopropyl | mp. 221.5–222.5° C. |
| 4 | Q12 | ethyl | ethyl | mp. 103–105° C. |
| 5 | Q14 | methyl | isopropyl | refractive index $n_{20}^D = 1.5154$ |
| 6 | Q14 | ethyl | isopropyl | mp. 96–99.5° C. |

SYNTHESIS EXAMPLE 2

[Synthesis of the Starting Material for Producing a Compound of Formula (I) (Synthesis of a Compound of Formula (II))]

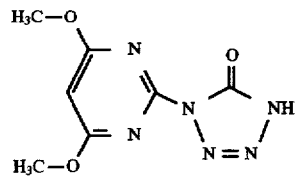

1-(4,6-Dimethoxy-2-pyrimidyl)-4-(2-methyl-1-propenyl)-5(4H)-tetrazolinone (1.4 g), sodium periodate (3 g) and osmium tetrachloride (0.1 g) were added to a mixed solution of water (30 ml) and 1,4-dioxane (80 ml), and the mixture was stirred at room temperature for one day. After the completion of the reaction, the reaction mixture was extracted with methylene chloride. The organic layer was then dried over anhydrous sodium sulfate, the solvent was distilled off, and the residue was subjected to silica gel column chromatography (eluant: chloroform/ethanol=10/1) to obtain 1-(4,6-dimethoxy-2-pyrimidyl)-5(4H)-tetrazolinone (0.8 g).

mp. 164.5°–165° C.

In analogous manner the following compounds were obtained:

1-(5-chloro-4-pyrimidyl)-5(4H)-tetrazolinone (mp. 131°–133° C.), 1-(4,6-dimethoxy-2-s-triazinyl)-5(4H)-tetrazolinone (mp. 86°–89.5° C.), and 1-(4,6-bis(dimethylamino)-2-s-triazinyl)-5(4H)-tetrazolinone (mp. 264°–265° C.).

SYNTHESIS EXAMPLE 3

(Synthesis of the starting material for Synthesis Example 2)

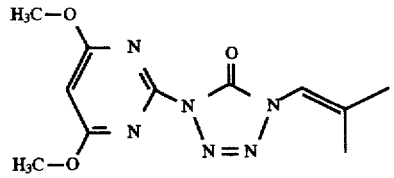

Sodium hydride (0.4 g, 60% in oil) was added to a mixture of 1-(2-methyl-1-propenyl)-5(4H)-tetrazolinone (1.4 g) and dimethylformamide (30 ml). After stirring for one hour, 4,6-dimethoxy-2-methylsulfonylpyrimidine (2.2 g) was added thereto, and the mixture was stirred at 80°–100° C. for 8 hours. The solvent was then distilled off under reduced pressure and the residue was subjected to silica gel column chromatography (eluant: chloroform/ethanol=15/1) to obtain 1-(4,6-dimethoxy-2-pyrimidyl)-4-(2-methyl-1-propenyl)-5(4H)-tetrazolinone (1.5 g).

mp. 84°–86° C.

In analogous manner, 1-(4,6-dimethoxy-s-triazinyl)-4-(2-methyl-1-propenyl)-5(4H)-tetrazolinone was obtained using 2-chloro-4,6-dimethoxy-s-triazine instead of 4,6-dimethoxy-2-methyl sulfonylpyrimidine.

mp. 127°–130° C.

1-(5-Chloro-4-pyrimidyl)-4-(2-methyl-1-propenyl)-5(4H)-tetrazolinone was obtained using 4,5- dichloropyrimidine instead of 4,6-dimethoxy-2-methylsulfonylpyrimidine. refractive index $n_{20}^D=1.5722$

REFERENCE EXAMPLE 1

(Synthesis of the Starting Material for Synthesis Example 3)

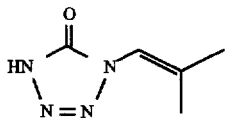

3,3-Dimethylacrylic acid chloride (3 g) was added dropwise to trimethylsilyl azide (11.5 g) under cooling with ice. After heating under reflux for 8 hours, the excess trimethylsilyl azide and the formed chlorotrimethylsilane were distilled off under reduced pressure. Methanol was added to the residue and the mixture was stirred. Thereafter, methanol was distilled off and the residue was subjected to silica gel column chromatography (eluant: chloroform/ethanol=15/1) to obtain 1-(2-methyl1-propenyl)-5(4H)-tetrazolinone (2.2 g).

mp. 74.5°–75° C.

SYNTHESIS EXAMPLE 4

[Synthesis of the Starting Material for Producing a Compound of Formula (I) (Synthesis of a Compound of Formula (II))]

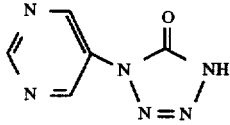

An ethyl acetate (60 ml) solution of 5-aminopyrimidine (2.85 g) was added dropwise to a mixture of diphosgene (6.0 g) and ethyl acetate (100 ml) under cooling with ice. After heating under refluxing for 6 hours, the solvent was distilled off under reduced pressure. The obtained residue and trimethylsilyl azide (11 g) were mixed and the mixture was heated under refluxing for 30 hours. The excess trimethylsilyl azide was distilled off under reduced pressure. Methanol was then added to the residue and the mixture was stirred. Thereafter, methanol was distilled off and the residue was subjected to silica gel column chromatography (eluant: chloroform/ethanol=15/1) to obtain 1-(5-pyrimidyl)-5(4H)-tetrazolinone (3.2 g).

mp. 211°–213° C.

SYNTHESIS EXAMPLE 5

[Synthesis of the Starting Material for Producing a Compound of Formula (I) (Synthesis of a Compound of Formula (II))]

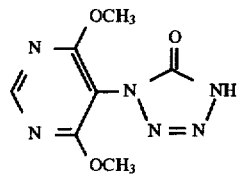

Thionyl chloride (2.4 g) was added dropwise to an anhydrous ether (50 ml) solution of 4,6-dimethoxypyrimidin-5-carboxylic acid (3.7 g) and anhydrous pyridine (1.6 g) under cooling with ice, and the mixture was stirred at the same temperature for 3 hours. After the precipitated pyridine hydrochloride was removed by filtration, the solvent was distilled off. To the obtained residue, trimethylsilyl azide (7 g) was added and the mixture was heated under refluxing for 30 hours. The excess trimethylsilyl azide was distilled off under reduced pressure. To the residue, methanol was added and the mixture was stirred. Thereafter, methanol was distilled off and the residue was subjected to silica gel column chromatography (eluant: chloroform/ethanol=15/1) to obtain 1-(4,6-dimethoxy-5-pyrimidyl)-5(4H)tetrazolinone (3.5 g).

mp. 172°–173.5° C.

BIOLOGICAL TEST EXAMPLES

Test Example 1

Test of pre-emergence soil-treatment against plowed land weeds

Preparation of Testing Solutions carrier: acetone, 5 parts by weight
emulsifier: benzyloxy polyglycol ether, 1 part by weight One part of an active compound and the above amounts of carrier and emulsifier are mixed to obtain a formulation of the active substance as an emulsion. A prescribed amount of this formulation is diluted with water to prepare testing solutions.

Testing Procedure

In the greenhouse, seeds of *Echinochloa crus-galli* and *Amaranthus lividus* were each sowed in the surface layer of plowed land soil filled in a 120 cm² pot with soil-covering, and a prescribed amount of the testing solution prepared by the above method was uniformly sprayed on the surface layer of soil in each testing pot. The herbicidal effect was evaluated 4 weeks after the sowing.

In this test, for example, the Compounds Nos. 2, 5 and 6 of the invention at 1.0 kg/ha exhibited 100% herbicidal activity against *Echinochloa crus-galli* and *Amaranthus lividus*.

Test Example 2

Test of post-emergence foliar application against plowed land weeds

Testing Procedure

In the greenhouse, seeds of *Echinochloa crus-galli* and *Amaranthus lividus* were each sowed in a 120 cm² pot filled with plowed land soil and covered with soil. At 10 days after the sowing and soil-covering (when the weeds were in 2-foliage period on average), a prescribed amount of the testing solution prepared similarly to those in the above Test Example 1 was uniformly sprayed on the foliage part of the test plant in each pot. At 3 weeks after the application, the herbicidal effect was evaluated.

In this test, the Compounds Nos. 5 and 6 of the invention at 2.0 kg/ha exhibited 90% or more of herbicidal activity against *Echinochloa crus-galli* and *Amaranthus lividus*.

Formulation Example 1

(Granules)

Water (25 parts) is added to a mixture of Compound No. 3 (10 parts) of the invention, bentonite (montmorillonite) (30 parts), talc (58 parts) and lignin sulfonate salt (2 parts) with well kneading and formed in 10–40 mesh granules using an extrusion-type granulator followed by drying at 40°–50° C. to give granules.

Formulation Example 2

(Granules)

A clay mineral (95 parts) having a particle size distribution of 0.2–2 mm is introduced in a rotary mixer and Compound No. 1 (5 parts) of the invention is sprayed therein with a liquid diluent under rotation to uniformly wet followed by drying at 40°–50° C. giving granules.

Formulation Example 3

(Emulsion)

An emulsion is obtained by mixing Compound No. 3 (30 parts) of the invention, xylene (5 parts), polyoxyethylene alkyl phenyl ether (8 parts) and calcium alkylbenzene sulfonate (7 parts) with stirring.

Formulation Example 4

(Wettable Powder)

A wettable powder is prepared by mixing Compound No. 5 (15 parts) of the invention, a mixture (1:5) of White Carbon (fine powder of hydrated non-crystalline silicon oxide) (80 parts) and powdery clay, sodium alkylbenzene sulfonate (2 parts) and a condensate of sodium alkylnaphthalene sulfonate and formaldehyde (3 parts) in a powdery state.

Formulation Example 5

(Wettable Granules)

Wettable granules are prepared by thoroughly mixing Compound No. 2 (20 parts) of the invention, sodium lignin sulfonate (30 parts), bentonite (15 parts) and calcined diatomaceous earth powder (35 parts) followed by addition of water and extrusion through a 0.3 mm screen and drying.

It will be understood that the specification and examples are illustrative but not limitative of the present invention and that other embodiments within the spirit and scope of the invention will suggest themselves to those skilled in the art.

We claim:
1. A compound of the formula

(I)

wherein
R$^1$ and R$^2$ each independently is C$_{1-4}$ alkyl, C$_{1-4}$ haloalkyl, cyclopropyl, cyclopentyl, cyclohexyl, C$_{2-4}$ alkenyl, C$_{2-4}$ haloalkenyl, C$_{3-4}$ alkynyl or phenyl or R$^1$ and R$^2$, together with the nitrogen atom to which they are bonded, form pyrrolidin-1-yl, 2,5-dimethyl pyrrolidin-1-yl, 3-pyrrolin-1-yl, 2,5-dimethyl-3-pyrrolin- 1-yl, piperidino, 2-methylpiperidino, 2,6-dimethylpiperidino, piperazin-1-yl, morpholino, 1,2,3,4-tetrahydroquinolin-1-yl or 2-methyl- 1,2,3,4-tetrahydroquinolin-1-yl, and R$^3$ is pyrimidinyl, pyrazinyl, pyridazinyl or 1,3,5-triazinyl, which may optionally be substituted by chlorine, C$_{1-4}$ alkyl, C$_{1-4}$ alkoxy, C$_{1-4}$ alkylthio, di(C$_{1-4}$ alkyl)amino or phenyl.

2. A compound according to claim 1, wherein
R$^1$ and R$^2$ each independently is C$_{1-4}$ alkyl, C$_{1-4}$ haloalkyl, cyclopropyl, cyclopentyl, cyclohexyl, C$_{2-4}$ alkenyl, C$_{2-4}$ haloalkenyl, C$_{3-4}$ alkynyl or phenyl, or R$^1$ and R$^2$, together with the nitrogen atom to which they are bonded, form pyrrolidin-1-yl, 2,5-dimethylpyrrolidin-1-yl, 3-pyrrolin-1-yl, 2,5-dimethyl-3-pyrrolin-1-yl, piperidino, 2-methylpiperidino, 2,6-dimethylpiperidino, piperazin-1-yl, morpholino, 1,2,3,4-tetrahydroquinolin-1-yl or 2-methyl-1,2,3,4-tetrahydroquinolin-1-yl, and R$^3$ is pyrimidinyl, pyrazinyl, pyridazinyl or 1,3,5-triazinyl, which may optionally be substituted by chlorine, methyl, methoxy, methylthio, dimethylamino or phenyl.

3. A compound according to claim 1, wherein such compound is 1-(5-pyrimidyl)-4-(N-ethyl-N-cyclohexyl-carbamoyl)-5(4H)-tetrazolinone of the formula 4. A compound according to claim 1, wherein such compound is 1-(4,6-dimethoxy-5-pyrimidyl)-4-(N-methyl-N-isopropyl-carbamoyl)-5(4H)-tetrazolinone of the formula 5. A compound according to claim 1, wherein such compound is 1-(4,6-dimethoxy-5-pyrimidyl)-4-(N-ethyl-N-isopropyl-carbamoyl)-5(4H)-tetrazolinone of the formula

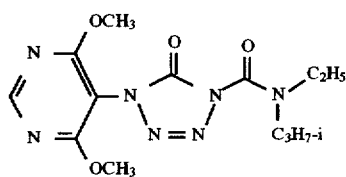

6. A herbicidal composition comprising a herbicidally effective amount of a compound according to claim 1 and a diluent.

7. A method of combatting unwanted vegetation which comprises applying to such vegetation or to a locus from which it is desired to exclude such vegetation a compound according to claim 1.

8. The method according to claim 7, wherein such compound is 1-(5-pyrimidyl)-4-(N-ethyl-N-cyclohexyl-carbamoyl)-5(4H)-tetrazolinone, 1-(4,6-dimethoxy-5-pyrimidyl)4-(N-methyl-N-isopropyl-carbamoyl)-5(4H)-tetrazolinone or 1-(4,6-dimethoxy-5-pyrimidyl)-4-(N-ethyl-N-isopropyl-carbamoyl)-5(4H)-tetrazolinone.

9. A compound of the formula:

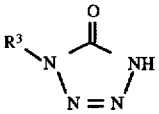

(II)

wherein $R^3$ is pyrimidinyl, pyrazinyl, pyridazinyl or 1,3,5-triazinyl, which may optionally be substituted by chlorine, $C_{1-4}$ alkyl, $C_{1-4}$ alkoxy, $C_{1-4}$ alkylthio, di($C_{1-4}$ alkyl)amino or phenyl.

10. A compound according to claim 9, wherein $R^3$ is pyrimidinyl, pyrazinyl, pyridazinyl or 1,3,5-triazinyl, which may optionally be substituted by chlorine, methyl, methoxy, methylthio, dimethylamino or phenyl.

* * * * *